United States Patent [19]
Abbott et al.

[11] Patent Number: 5,385,540
[45] Date of Patent: Jan. 31, 1995

[54] CARDIOPLEGIA DELIVERY SYSTEM

[75] Inventors: Martyn S. Abbott, Richardson; Thomas C. Thompson; Kenneth A. Jones, both of McKinney; Albert M. Davis; Andrew P. Mattson, both of Richardson, all of Tex.

[73] Assignee: Quest Medical, Inc., Allen, Tex.

[21] Appl. No.: 67,683

[22] Filed: May 26, 1993

[51] Int. Cl.$^6$ .................. A61M 37/00; A61M 31/00; A61M 1/00

[52] U.S. Cl. .......................... 604/4; 604/65; 604/67; 604/113; 604/151; 604/153; 128/DIG. 3

[58] Field of Search ............. 604/4, 27, 29, 65, 67, 604/113, 131, 151, 153; 128/DIG. 3, DIG. 12

[56] References Cited

U.S. PATENT DOCUMENTS

| T994,001 | 5/1980 | Buckberg et al. | 128/214 R |
|---|---|---|---|
| 4,236,880 | 12/1980 | Archibald | 417/478 |
| 4,416,280 | 11/1983 | Carpenter et al. | 128/399 |
| 4,464,172 | 8/1984 | Lichtenstein | 604/65 |
| 4,466,804 | 8/1984 | Hino | 604/4 |
| 4,479,761 | 10/1984 | Bilstad et al. | 417/395 |
| 4,568,330 | 2/1986 | Kujawski et al. | 604/53 |
| 4,657,490 | 4/1987 | Abbott | 417/478 |
| 4,696,671 | 9/1987 | Epstein et al. | 604/67 |
| 4,821,761 | 4/1989 | Aid et al. | 137/101.21 |
| 4,874,359 | 10/1989 | White et al. | 604/4 |
| 4,883,455 | 11/1989 | Leonard | 604/4 |
| 5,171,212 | 12/1992 | Buck | 604/4 |
| 5,322,500 | 6/1994 | Johnson et al. | 604/4 |

OTHER PUBLICATIONS

Warm Induction of Cardioplegia with Glutamate-Enriched Blood in Coronary Patients with Caridiogenic Shock Who are Dependent on Inotropic Drugs and Intra-Aortic Balloon Support—Eliot R. Rosenkrantz, M.D. et al., *The Journal of Thoracic and Cardiovascular Surgery*, 86:507–518, 1983.

Retrograde Coronary Sinus Perfusion: A Safe Alternative for Ensuring Cardioplegic Delviery in Aortic Valve Surgery—Philippe Menasche, M.D., et al., The Annals of Thoracic Surgery, vol. 34, No. 6, Dec. 1982, pp. 647–658.

Myocardial Protection During Surgical Coronary Reperfusion—Eliot R. Rosenkranz, M.D. et al., *The American College of Cardiology*, 1983:1(5):1235–46.

Benefits of Normothermic Induction of Blood Cardioplegia in Energy depleted Hearts, with Maintenance of Arrest by Multidose Cold Blood Cardioplegic Infusions—Eliot R. Rosenkranz, M.D., et al., *The Journal of Thoracic and Cardiovascular Surgery*, 84:667–677, vol. 84, No. 5, Nov., 1982.

Comparison of Distribution Beyond Coronary Stenoses of Blood and Asanguineous Cardioplegic Solutions—John M. Robertson, M.D., et al., *The journal of Thoracic and Cardiovascular Surgery*, vol. 86, No. 1, Jul. 1983, pp. 80–86.

Advantages of Blood Cardioplegia Over Continuous Coronary Perfusion or Intermitten Ischemia—David M. Follette, M.D., et al., *The Journal of Thoracic and Cardiovascular Surgery*, vol. 76, No. 5, Nov. 1978, pp. 604–619.

(List continued on next page.)

*Primary Examiner*—Corrine Maglione
*Attorney, Agent, or Firm*—Ross, Howison, Clapp & Korn

[57] ABSTRACT

A cardioplegia system for delivering cardioplegic solution to the heart during open heart surgery in cooperation with an extracorporeal blood circuit employing a heart/lung machine, includes a conduit diverting a portion of the blood flow from the heart/lung machine to a cardioplegia delivery line. A heat exchanger for controlling fluid temperature is provided in the cardioplegia delivery line. A first pump combines the blood from the conduit with a second fluid and delivers the combined flow into the delivery line leading to the heat exchanger. A control panel is operatively connected for adjusting the ratio of blood and second fluid delivered by the first pump and for adjusting the total volumetric rate of flow from the first pump.

69 Claims, 4 Drawing Sheets

OTHER PUBLICATIONS

Clinical Evaluation of the Relative Effectiveness of Multidose Crystalloid and Cold Blood Potassium Cardioplegia in Coronary Artery Bypass Graft Surgery; A Nonrandomized Matched-Pair Analysis—Arthur J. Roberts, M.D., et al., *The Annals of Thoracic Surgery*, vol. 33, No. 5, May 1982, pp. 421-433.

"Continuous Normothermic Blood Cardioplegia: Simplified Delivery Circuit", Ponangi V. Satyanarayana, et al., *Annual Thoracic Surgery*, 1992; 54:809-16.

"Minimal Hemodilution and Optimal Potassium Use During Normothermic Aerobic Arrest", Daniel Le Houerou, et al., Annual Thoracic Surgery, 1992; 54:809-16, pp. 815-816.

"Simplified Method for Delivering Normothermic Blood Cardioplegia", Philippe Menasche, MD, PhD, et al., The Society of Thoracic Surgeons, 1993; 55:177-8.

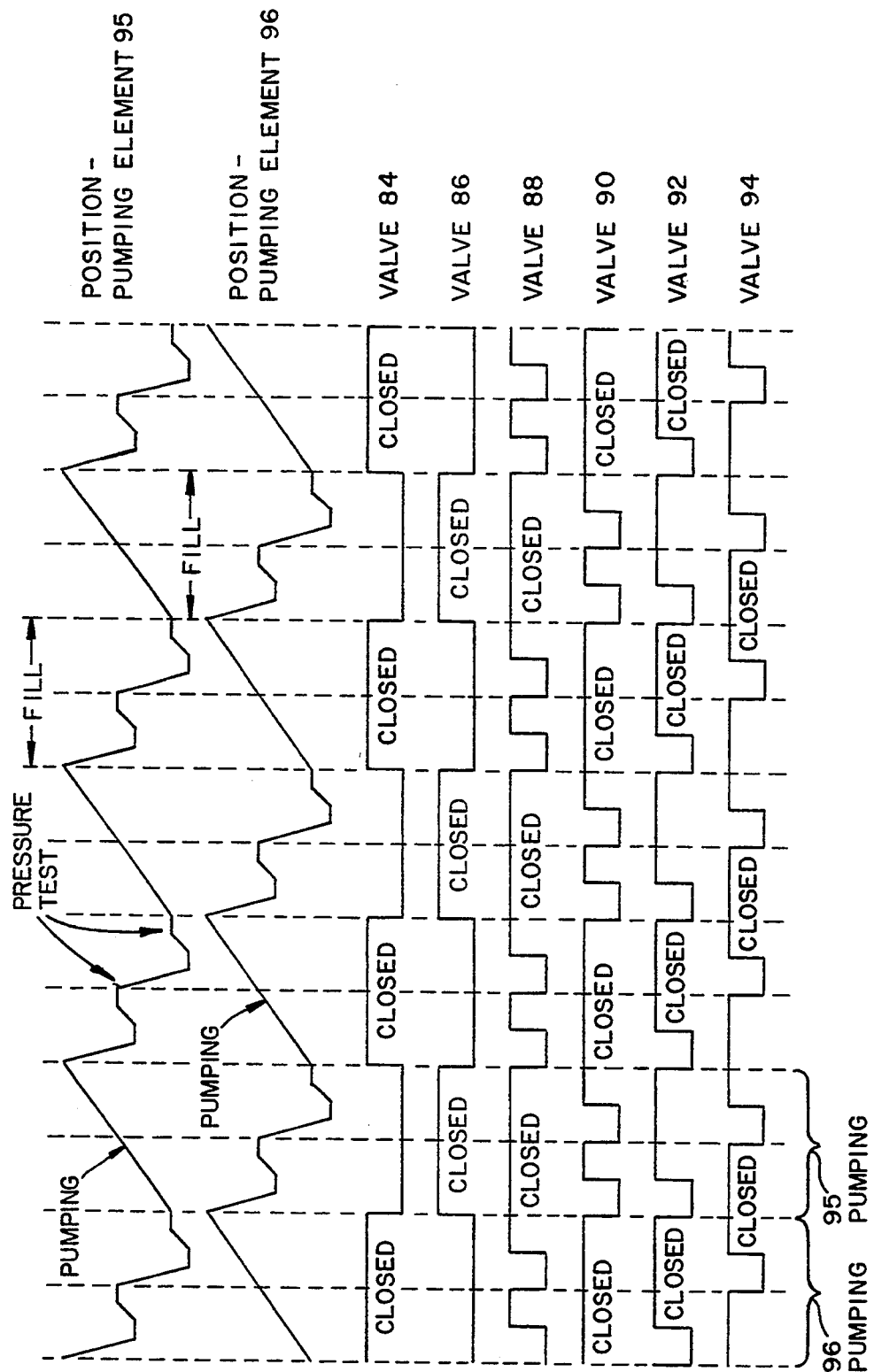

CARDIOPLEGIA DELIVERY SYSTEM

TECHNICAL FIELD OF THE INVENTION

This invention relates to fluid delivery systems, and more particularly to systems for the delivery of multiple fluids in a cardioplegia circuit to support a patient's heart during open heart surgery.

BACKGROUND OF THE INVENTION

In the performance of open heart surgery, the patient is supported by an extracorporeal blood circuit employing a heart/lung machine. The heart is isolated from the vascular system, and venous blood is diverted into the extracorporeal blood circuit where it is oxygenated, temperature-controlled and returned to the patient's arterial side. A separate circuit is established for supplying a cardioplegic solution to the heart as the surgery proceeds.

The cardioplegia circuit functions to still the heart, lower the metabolic requirements of the heart, protect the heart during periods of ischemia, and, finally, prepare the heart for reperfusion at the end of the procedure. Operation of the extracorporeal blood circuit as well as the cardioplegia delivery is performed by a trained perfusionist under the direction of the surgeon. The principal elements of cardioplegia solution are blood, representing a small fraction diverted from the output of the heart/lung machine, combined with a crystalloid solution. In addition, a minor but critical amount of potassium solution is added to the cardioplegic flow to still the heart.

Depending upon the requirements of the particular surgery, the cardioplegia solution may be cooled or warmed, and may be delivered in antegrade fashion to the aortic root or coronary ostia, or in a retrograde mode to the coronary sinus. The requirements placed upon the cardioplegic solution vary as the surgery proceeds, and are subject to the clinical judgment of individual surgeons.

A typical cardioplegia delivery system employs two tubes routed through a single rotary peristaltic pump to forward both the separate blood and crystalloid solutions to a Y combining the two into a single flow. The ratio between the blood and crystalloid solution is determined simply by the relative diameters of the tubing carrying the two solutions, since each is mounted on the same rotary peristaltic mechanism and thus is forwarded by the same action. The tubing is usually provided in a 4:1 ratio of blood to crystalloid cross-sectional flow area, so that the rotary peristaltic pump is delivering blood and crystalloid to the delivery line in a ratio of approximately 4:1. Potassium is typically provided to the delivery line upstream of the pump from two alternate crystalloid solutions containing potassium, one having a relatively low concentration of potassium, the other a higher concentration. The perfusionist selects between the two sources as monitoring of the patient's condition indicates. The higher potassium concentration is utilized to arrest the heart, while the lower is used to maintain the stilled condition. The clinical team must provide sufficient potassium in the cardioplegia solution to establish the stilled condition of the heart and maintain it during the procedure, while avoiding the risks associated with hyperkalemia which may result from excessive potassium.

Existing systems for delivery of cardioplegia are characterized by poor adaptability to varying requirements which the surgeon in charge may place upon the system as to ratios of the principal ingredients in the cardioplegia flow and as to temperature control. The systems have particularly poor control over the cardioplegia delivery at low flow rates. Moreover, the shearing forces to which the blood in the cardioplegia line is subjected by peristaltic action risks damage to the blood.

SUMMARY OF THE INVENTION

In accordance with the invention, there is provided a cardioplegia system for delivering cardioplegic solutions to the heart during open heart surgery which cooperates with an extracorporeal blood circuit employing a heart/lung machine. The system includes a conduit for diverting a portion of the blood flow from the heart/lung machine to a cardioplegia delivery line. A heat exchanger for controlling fluid temperature is provided in the cardioplegia delivery line. A first pump combines blood from the conduit with a second fluid, and delivers the combined flow into the delivery line leading to the heat exchanger. A second pump is provided for delivering a third fluid into the delivery line downstream from the first pump at a flow rate less than 10% of the flow rate of the combined output of the first pump.

The invention further includes control means for adjusting the ratio of blood and second fluid delivered by the first pump, for adjusting the total volumetric rate of flow from the first pump, and for controlling the operation of the second pump so that the volumetric rate of flow of the third fluid is maintained at a selected percentage of the flow rate from the first pump.

In a preferred mode, the first pump preferably employs two pumping chambers, so that one chamber may be refilled while the other is emptying, whereby substantially continuous flow from the first pump may be achieved. The second pump is preferably a positive displacement pump, either a syringe or a volumetric pouch configuration containing potassium solution driven at a rate controlled by the control means. The output of the second pump joins the delivery line downstream from the first pump.

In a specific embodiment, the heat exchanger has the ability to both heat and cool the cardioplegic solution, and operates under the control of the control means. Preferably, the first pump includes at least one disposable in-line bladder and a Separate drive means for changing the volume of the bladder. In the preferred embodiment, a fill cycle of the first pump comprises two separate time segments, including a first period for introduction of blood from the main extracorporeal blood circuit and a second period for the introduction of a second fluid, whereby the blood and the second fluid are combined in the bladder in a selected ratio before being forwarded from the first pump. Also preferably the pressure of the cardioplegia solution is sensed, monitored, and controlled by the control means within safe operating limits.

According to another aspect of the invention, all of the major operating conditions of a cardioplegia system including the desired volumetric rates, the desired ratios and percentages of blood, second fluid, third fluid, and any additional fluids, the output temperature and heating and cooling of the output fluid as well as the appropriate operating pressures and safety pressure conditions for either antegrade or retrograde cardioplegia are conveniently controlled from a centralized operator control panel connected to the cardioplegia system through a microprocessor control section. This advantageously frees perfusionist, surgeons and other healthcare professionals performing delicate medical procedures, from the complex, cumbersome and sometimes confusing manual rigging, connecting, heating, cooling, monitoring and adjusting of all the various aspects of the prior cardioplegia systems. The centralized control results in increased safety and quality of cardioplegia fluid delivery. The system is easily adaptable and adjustable to the particular requirements of a given patient. The system may also be adaptable for blood fluid delivery for other clinical applications and healthcare procedures in which multifluid pumping systems may be desirable or beneficial.

BRIEF DESCRIPTION OF THE DRAWINGS

For a more complete understanding of the present invention and for further advantages thereof, reference is now made to the following Description of the Preferred Embodiments taken in conjunction with the accompanying Drawings in which:

FIG. 6 is a timing diagram illustrating the cycle of the blood/crystalloid pump depicted in FIGS. 2–5.

DESCRIPTION OF THE PREFERRED EMBODIMENTS

Figure 1:
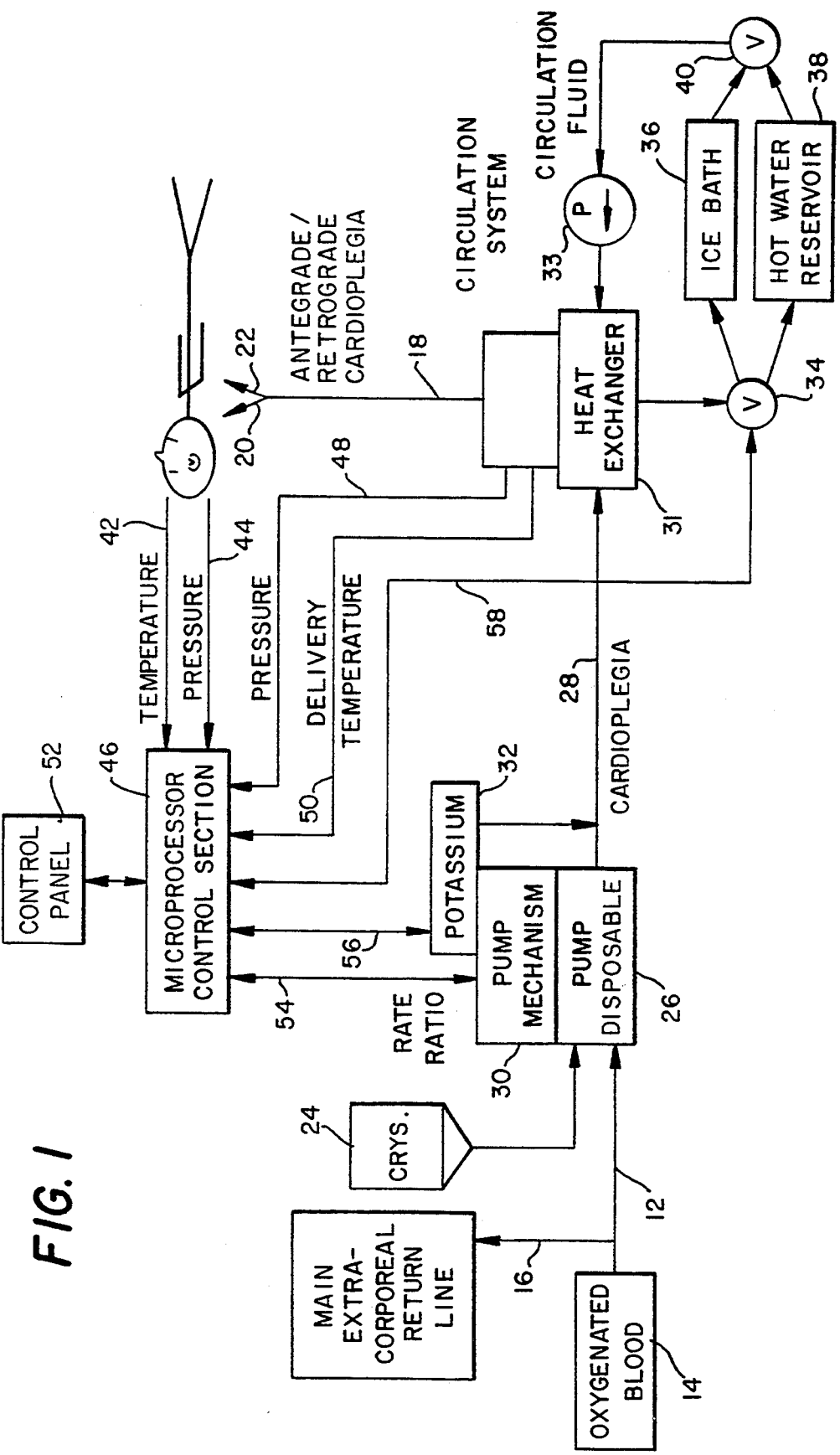
FIG. 1 is a schematic diagram of a cardioplegic delivery system embodying the invention.

As depicted in FIG. 1, a cardioplegia delivery system 10 is established to provide solution to the heart of a patient during open heart surgery. The principal component of the cardioplegic solution is blood delivered to the system through conduit 12 which is connected to the output of the oxygenator 14 of the heart/lung machine sustaining the patient's vascular system while the heart is isolated therefrom during surgery. Oxygenator 14 provides arterial blood in the main extracorporeal circuit through a return line 16 to the patient's aorta. A fraction, usually about 10%, of the heart/lung machine output is diverted into conduit 12 for processing by the cardioplegic circuit and forwarding to the patient's heart through cardioplegia delivery line 18. The cardioplegic solution flowing through line 18 may be delivered through antegrade line 20 to the aortic root, or through retrograde line 22 to the coronary sinus.

A crystalloid solution is stored in container 24 for combination with blood flowing in line 12 in a disposable pumping cassette 26. The output of cassette 26 is supplied through line 28 to a heat exchanger 31. Pump cassette 26 is controlled by an electromechanical pump mechanism 30 in which cassette 26 is mounted. A second pump 32 containing potassium solution supplies its output to line 28 downstream from the pump cassette 26.

Preferably, pump 32 may be a syringe pump or a volumetric pouch of a type well known in the infusion art. In the case where pump 32 is a syringe pump, the potassium solution may be loaded into a syringe, and the syringe mounted in pump 32 which progressively depresses the syringe plunger to deliver potassium solution to line 28. The flow rates of potassium solution are less than about 10%, and preferably less than about 5%, of the total flow rate issuing from pump cassette 26. An accurately controllable pump, such as a syringe pump, may be advantageously used in applications where a particular fluid additive or constituent must be a carefully controlled small portion, less than about 10%, of the total flow volume.

In the heat exchanger 31, the cardioplegic solution is juxtaposed with a circulating temperature controlled fluid to adjust the temperature of the solution prior to forwarding the solution to the heart through line 18. Preferably pump 33 circulates temperature controlled fluid through the heat exchanger 31 either by push or pull. FIG. 1 depicts a push through coolant system in which a pump 33 circulates the control fluid through heat exchanger 31 and then to a two-way valve 34, which valve 34 may direct the circulating fluid either to an ice bath 36 for cooling or a heated water reservoir 38 for heating. The circulating fluid is then pumped via valve 40 back through the heat exchanger 31 where the cardioplegia solution receives heating or cooling without contamination across a sealed heat transfer material or membrane within the heat exchanger 31.

The system includes patient monitoring of myocardial temperature along the signal path 42 and heart pressure along signal path 44 communicating to a central microprocessor control section 46. In addition, the pressure and temperature of the cardioplegic solution in delivery line 18 is sensed and the data is forwarded along signal paths 48 and 50 to the control microprocessor 46. Data input to microprocessor 46 through control panel 52 may include an advantageous combination of the following parameters:

1. Desired overall volumetric flow rate through disposable pump cassette 26;
2. Desired blood/crystalloid ratio to be forwarded by disposable pump cassette 26.
3. Desired potassium concentration to be established by pump 32.
4. Desired temperature of solution in cardioplegia delivery line 18 or desired patient temperature.
5. Safety parameters such as the pressure of the cardioplegia solution in the system or in the patient.

In response to the data input through the control panel 52 and the monitored conditions along signal paths 42, 44, 48 and 50, microprocessor control section 46 controls the operation of pump mechanism 30 via signal path 54, and of potassium syringe pump 32 by signal along path 56. In addition, microprocessor control section 46 controls the circulation of fluid in the heat exchanger circulation path along signal path 58 either for obtaining a desired patient temperature or a desired output solution temperature. Further, the safety parameters such as pressure limits for a particular procedure or a particular patient may be controlled based upon input settings or based upon preset standards, as for example, one range of acceptable pressure limits for antegrade and another range for retrograde cardioplegia.

In accordance with the invention, the microprocessor controller section 46 controls the pump mechanism 30 to combine crystalloid from container 24 and blood from line 12 in any selected ratio over a broad range of blood/crystalloid ratios. The controller 46 may command the pump mechanism 30 to deliver blood without crystalloid addition. A preferred range for the blood/crystalloid ratio adjustment capability is from 0 to 20:1. The rate of flow produced by the pump mechanism 30 of the combined output from disposable pump cassette 26 is preferably variable from 0 to 500 milliliters per minute. The pump mechanism 30, may be operated by microprocessor 46 in either a continuous or intermittent mode by instruction through control panel 52. The potassium syringe pump 32 is automatically controlled to deliver at a rate such that the introduction of potassium solution to line 28 is automatically maintained at the selected concentration vis-a-vis the flow of disposable cassette 26, without regard to changes requested in the flow rate from pump cassette 26 or changes in the blood/crystalloid ratio, requested of the pump mechanism 30 through microprocessor 46.

Figure 2:
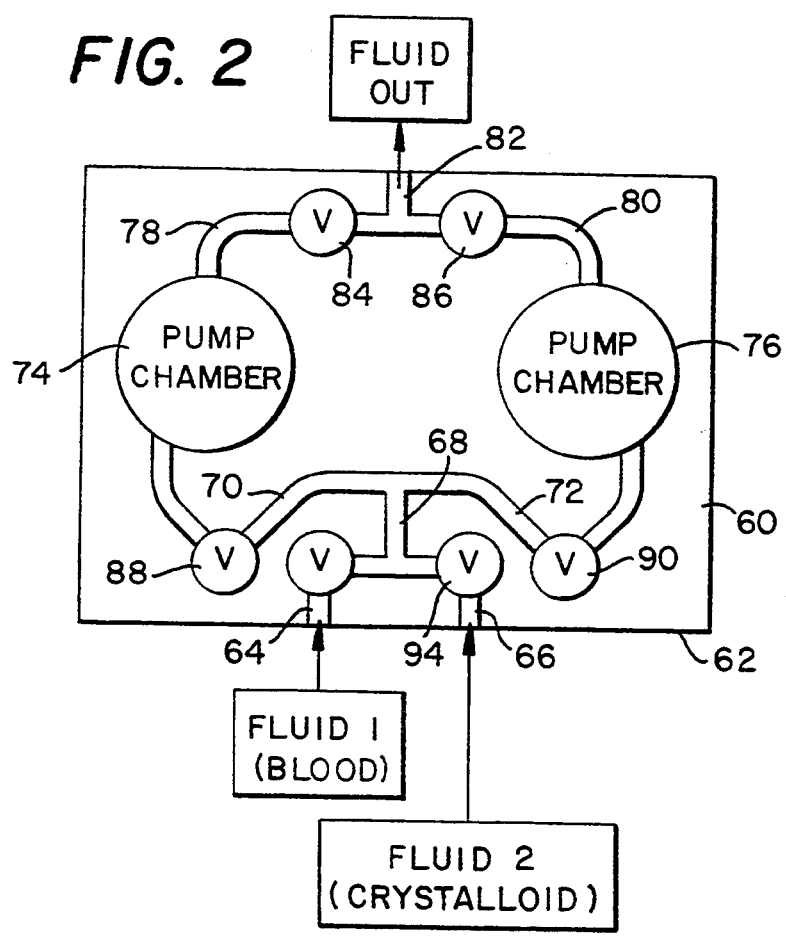
FIG. 2 is a plan view of a disposable pump cassette for a blood/crystalloid combining pump which may be used in the system of FIG. 1.

Disposable pump cassette 26 is illustrated in FIG. 2. The cassette may be formed from two flexible plastic sheets 60 bonded together selectively to form open flow paths and chambers therebetween. Each sheet 60 may be of any simple flexible material such as polyvinylchloride, and the sheets may be radio frequency welded together, leaving the flow paths and pump chambers unbonded. A bladder cassette of this type advantageously reduces the shearing forces and potential damage to which blood might be subjected in other pumps, such as peristaltic pumps.

The entry side 62 of cassette 26 includes a blood inlet 64 and a crystalloid inlet 66. Inlets 64 and 66 lead to a common pump inlet path 68, which is bifurcated to form pump flow paths 70 and 72. Flow path 70 leads to enlarged fluid bladder pump chamber 74 and path 72 leads to an identical fluid bladder pump chamber 76. Outlet path 78 from pump chamber 74 and outlet path 80 from pump chamber 76 are joined at a common outlet 82 from cassette 26 for delivery of the mixed cardioplegic solution to line 28.

FIG. 2 depicts six valve sites located along the fluid paths in cassette 26. These are sites at which the corresponding flow path may be occluded through operation of a valve plunger on the pump mechanism 30, to press the sheets 60 together at the valve, when the cassette 26 is mounted in operating position in the mechanism 30. Valve 84 is positioned to occlude the outlet path 78 from pump chamber 74. Valve 86 is positioned to occlude outlet path 80 from pump chamber 76. Bladder inlet valves along pump chamber inlet paths 70 and 72 are identified by reference numerals 88 and 90, respectively. Valves 92 and 94 for controlling the passage of blood or crystalloid alternately to common inlet path 68 are positioned at inlets 64 and 66, respectively.

Figure 3:
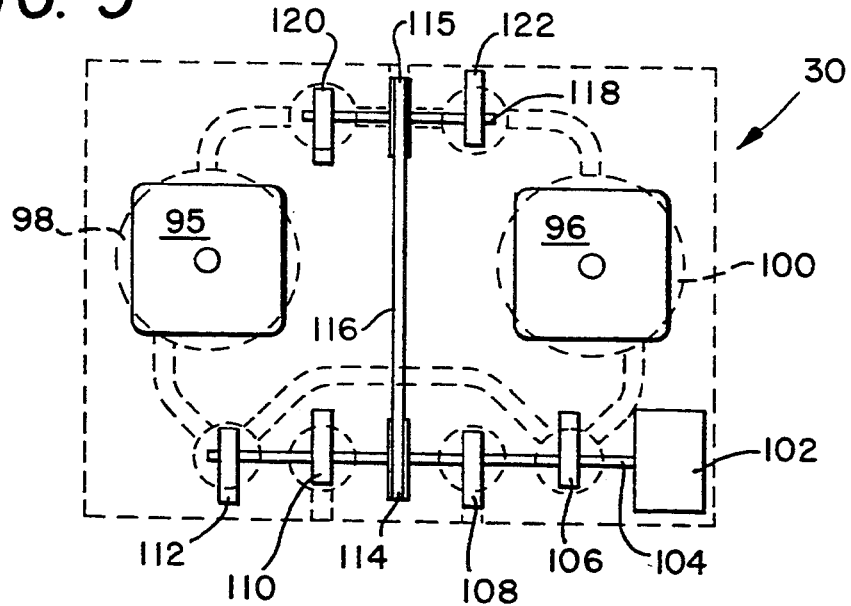
FIG. 3 is a plan view of a pump mechanism for operation of the cassette of FIG. 2.

Pump mechanism 30 is illustrated in FIG. 3, and incorporates a pair of pumping motors 95 and 96. Pumping motor 95 is positioned to advance and retract a bladder driving element 98, and pumping motor 96 is positioned to similarly operate a second bladder driving element 100. Valve cam motor 102 is provided to operate all valve closures on the disposable cassette 26. Cam motor 102 turns an inlet cam shaft 104 carrying valve cams 106, 108, 110 and 112. Cam shaft 104 also turns, by means of pulleys 114 and 115 and timing belt 116, an outlet cam shaft 118. Outlet cam shaft 118 carries valving cams 120 and 122.

Figure 4:
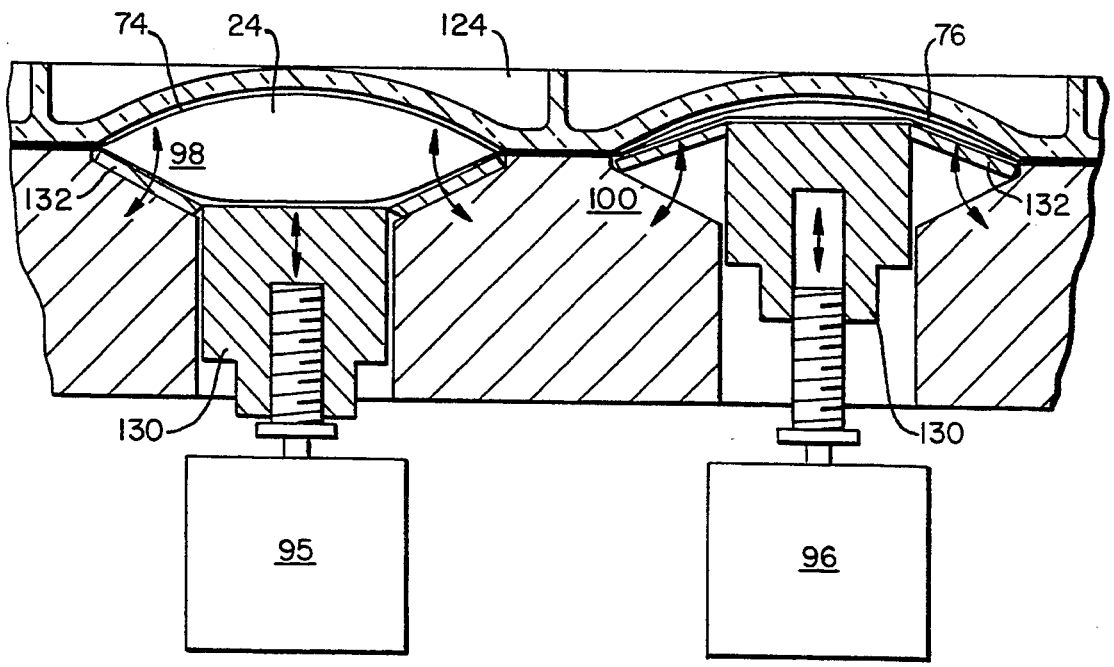
FIG. 4 is a schematic illustration of the functioning of the two pump chambers of FIG. 2.

As best seen in FIG. 4, disposable cassette 26 is positioned tightly against the face of mechanism 30 by a closing door 124 so that the cassette bladder pumping chambers 74 and 76 are enclosed, and confront driving elements 98 and 100. Driving elements 98 and 100 may be of identical construction, and preferably of the petal module type disclosed in U.S. Pat. No. 4,657,490, the disclosure of which is incorporated herein by reference. Although driving elements of this petal module type have the advantage of a linear relationship between displacement by the pump motor and volumetric displacement from the pump chamber, by their close compliance and confrontation to the plastic disposable cassette and by reduced shearing forces associated with the smooth pump action, other driving elements which provide a predictable volumetric displacement by a given advancement of the motor might be utilized.

The petal module type of driving element illustrated includes a hub 130, surrounded by radially extending, pivotally mounted petals 132 so that the hub 130 together with the petals 132 provides a confronting surface for the confined pump chamber. Advancement of motor 95 or 96 causes its hub 130 to advance and carry the petals 132 along with it for reducing the volume of the confined pump chamber. Conversely, retraction of motor 95 or 96 causes the corresponding driving element 98 or 100 to retract, withdrawing the constraint on chamber volume.

In FIG. 4, element 98 is illustrated substantially fully retracted, so that pump chamber 74 is filled with fluid, and element 100 is pushed to its full advancement, emptying its pumping chamber 76. Means for measuring the force required to advance each motor, or a pressure sensor contacting the cassette 26 (not shown) is also provided to enable microprocessor 46 to record data representative of the pressure on each bladder chamber.

Figure 5:
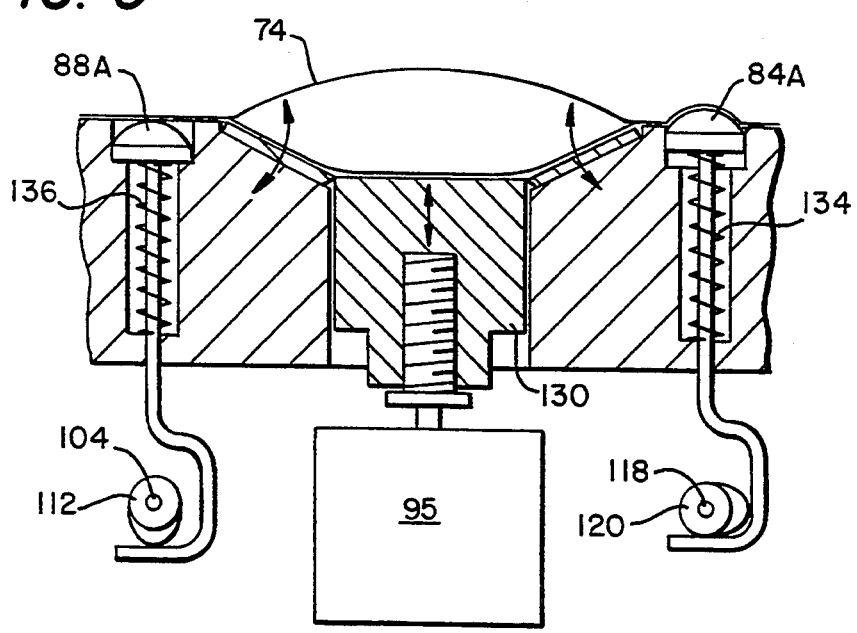
FIG. 5 is a schematic illustration of one pump driver and associated valving mechanisms of the mechanism of FIG. 3.

FIG. 5 illustrates the valving action embodied in mechanism 30, by showing the inlet and the outlet valve arrangement from a single pump chamber. All six valves (90, 94, 92, 88, 84 and 86) and their respective valve cams (106, 108, 110, 112, 120 and 122) operate in similar fashion. Driving element 130 engages the disposable pump chamber 74. Inlet plunger valve 88A and outlet plunger valve 84A, controlled by cams 112 and 120 are normally closed by the action of biasing springs 134 and 136. In the closed condition dictated by the biasing springs, each valve plunger presses against its corresponding valve site on disposable cassette 26 closing the corresponding fluid path. The valve sites 84–94 are each provided with a similar, normally-closed valve. Each of the valve sites 84–94 is opened under the action of valve camming motor 102 upon rotation of its corresponding cam to an open position, retracting the valve plunger from the disposable cassette, and opening the corresponding flow path flow. In FIG. 5, cam 112 has moved to the open position, retracting valve plunger 88A to open valve 88 on cassette 26, opening the inlet 70 of bladder 74 for entrance of fluid.

FIG. 6 illustrates the a timing diagram for the operation of the valve cam motor 102 in conjunction with the pumping motors 95 and 96. In the cycle described, one chamber pumps a mixture of blood and crystalloid in a selected ratio outwardly from outlet 82 of cassette 26, while the other pumping chamber is undergoing a sequential fill and test protocol. Filling chamber is filled with blood to the volume to produce the desired ratio followed by pressure testing of the chamber with its inlet and outlet valves closed to verified capture of the desired amount of blood. Following this step, the drive element of the filling pumping chamber is further retracted and crystalloid solution admitted to complete the filling of the chamber. Then the inlet and outlet valves on the filling chamber are closed to pressure test the chamber for a captured full load. Additional pressure tests and monitoring may be conducted during pumping to determine if there is any unsafe occlusion or to control the pressure within an appropriate safe range for a given procedure.

Thus, at the commencement of the FIG. 6 diagram, the pumping chamber bladder 74 has been emptied, and the other bladder 76 is full of a blood-crystalloid mixture in the desired proportions. The outlet valve 84, from chamber 74 is closed. Outlet valve 86 is open to pass the combined fluid from chamber 76 through the outlet 82 to the heat exchanger 31 at the requested volumetric flow rate. Throughout the period of delivery from chamber 76, its inlet valve 90 remains closed, and the corresponding pumping element 100 is advanced by motor 96 to reduce the volume of bladder 76 to expel the blood/crystalloid solution. The speed of motor 90 is governed by the requested flow rate. The outlet valve 84 from chamber 74 remains closed throughout this period of pumping from chamber 76.

The valves 92 and 94 controlling inlet of blood and crystalloid to common inlet path 68, and the inlet valve for chamber 74 are sequentially opened and closed during the filling protocol for bladder 74, which occupies the time period during which bladder 76 is delivering fluid to line 28. Thus, when one bladder has completed its pumping step, the other has received solution constituents in the desired ratio and is ready to deliver. Substantially continuous flow is thus enabled.

In the 4-step filling protocol for chamber 74, illustrated at the outset of the diagram, valves 92 and 88 are initially open, and valve 94 closed. Thus, an open flow path for entry of blood to chamber 74 is provided through inlet 64, common path 68 and pump chamber inlet path 70, while crystalloid is occluded at valve 94. Pump motor 95 is retracted sufficiently to admit sufficient blood to comprise the desired fraction of total chamber volume. Then valves 92 and 88 are closed, and pump motor 95 is advanced a few steps, to confirm by elevating pressure that the requested blood load has been captured between closed valves 88 and 94. With confirmed introduction of the correct amount of blood, valves 88 and 94 are opened while valve 92 remains closed to stop further blood entry. The pump motor 95 now retracts to admit the correct volume of crystalloid along paths 66, 68 and 70. This is followed by closing valves 88 and 94. Motor 95 is advanced briefly to confirm by pressure elevation that the full incremental volume has been occupied by crystalloid solution. With this confirmation, the fill protocol is complete, and chamber 74 is ready for delivery on the completion of delivery from chamber 76. As chamber 74 then delivers, chamber 76 undergoes a similar 4-step filling protocol.

It will be appreciated that a change in blood/crystalloid ratio is a simple adaptation for the pump mechanism 30. In the diagram, the retraction of the pumping element during blood fill and crystalloid fill is depicted as substantially equal. If a different ratio is requested through control panel 52, microprocessor 46 simply directs the motors 95 and 96 to retract by different amounts during their blood-fill and crystalloid-fill steps. The full retraction of a motor is the same for the combined fill. It is simply necessary to adjust the amount of retraction during each fill step to the requested ratio. The ratio may be continuously adjusted from 100% of blood to 100% crystalloid. Thus, if the requested blood/crystalloid ratio is R, and the motor driven-volume displacement relationship is linear, $$R = \frac{\text{Number of motor steps retracted during blood fill}}{\text{Number of motor steps retracted during crystalloid fill}}$$

The total volumetric flow rate from the cassette is varied pursuant to operator request simply by compressing or expanding the time for a cycle to be completed. Of course, if intermittent operation is desired, this may be provided as well.

No matter what changes may be made to the blood/crystalloid flow rate, microprocessor 46 preferably automatically controls potassium pump 32 to deliver at a ratio which provides the requested percentage of the blood/crystalloid flow.

The improved and simplified control over cardioplegia enabled by this invention, and improved solution handling, are believed to represent a significant tool specifically for the heart surgeon/perfusionist team, as well as for other healthcare teams which may require controlled pumping or recirculation of blood mixed with one or more other fluids. Although the present invention has been described with respect to specific embodiments thereof, it will be understood that various changes and modifications will be suggested to one skilled in the art and it is intended to encompass such changes and modifications as fall within the scope of the appended claims.

We claim:

1. A clinical multi-fluid pumping system comprising:
   (a) a first pump for combining a first fluid containing blood and a second fluid, metered from two separate sources, and pumping the combined flow into a patient delivery line, said pump comprising a pump chamber for receiving and combining said first and second fluids having an inlet and an outlet and drive means for varying the volume of the pump chamber; and
   (b) control means for: adjusting the ratio of the first and second fluids combined by the first pump and adjusting the total volumetric rate of flow from the first pump.

2. The system of claim 1, wherein said first pump employs two pumping chambers, so that one chamber may be refilled while the other is emptying, whereby substantially continuous flow from the first pump may be achieved.

3. The system of claim 1 in which a third fluid is to be added to the patient delivery line, and further comprising a second pump delivering the third fluid to the patient delivery line under control of the control means.

4. The system of claim 3 wherein said control means automatically adjusts the delivery rate of the second pump in response to changes in the flow rate requested from the first pump, in order to maintain a selected concentration of third fluid in the delivery line.

5. The system of claim 4, wherein the control means operates, upon selection by the user of a volumetric flow rate from the first pump, to establish the flow rate of the second pump.

6. The system of claim 3, wherein the output of the second pump joins the delivery line downstream from the first pump.

7. The system of claim 1, further comprising a heat exchanger which includes means for both heating and cooling the output of the first pump, and the control means also controls the heating and cooling means.

8. The system of claim 1, wherein the first pump comprises an in-line bladder and the drive means changes the volume of the bladder.

9. The system of claim 1, wherein said control means controls the first pump to provide a fill cycle for filling the pump chamber of the first pump which cycle comprises two separate time segments including a first period for introduction of blood from the conduit and a second period for introduction of the second fluid, whereby the blood and second fluid are combined in the bladder in a selected ratio before being forwarded from the first pump.

10. The system of claim 1, further comprising a heat exchanger receiving the combined flow from the first pump, wherein the control means operates upon selection by the user of a desired temperature to adjust the heating and cooling of the combined flow in the heat exchanger to obtain the selected desired temperature.

11. The system of claim 61, wherein the control means operates to monitor pressure resulting from the cardioplegic solution so that the monitored pressure is maintained within selected or predetermined pressure limits.

12. A cardioplegia system for delivering cardioplegic solution comprising blood and at least a second fluid to the heart through a cardioplegia delivery line during open heart surgery in cooperation with an extracorporeal blood circuit employing a heart/lung machine serving as a source for blood, and with a second source for said second fluid, comprising:
  (a) a conduit diverting a portion of the blood flow from the heart/lung machine to the cardioplegia delivery line;
  (b) a pump having a pump chamber with an inlet and an outlet, said pump having means for metering blood from the conduit into the pump chamber and combining it in an adjustable ratio with a second fluid metered by the pump from said second source into the pump chamber, and delivering the combined flow into the delivery line; and
  (c) control means for adjusting the ratio of blood and second fluid delivered by the pump and for adjusting the total volumetric rate of flow from the pump.

13. The system of claim 12, wherein said pump employs two pumping chambers, so that one chamber may be refilled while the other is emptying, whereby substantially continuous flow from the pump may be achieved.

14. The system of claim 12, in which a third fluid is to be added to the cardioplegic solution and further comprising a second pump delivering the third fluid to the cardioplegia delivery line under control of the control means.

15. The system of claim 14 wherein said control means automatically adjusts the delivery rate of the second pump in response to changes in the flow rate requested from the pump, in order to maintain a selected concentration of third fluid in the delivery line.

16. The system of claim 15, wherein the control means operates, upon selection by the user of a volumetric flow rate from the pump, to establish the flow rate of the second pump.

17. The system of claim 14, wherein the output of the second pump joins the delivery line downstream from the pump.

18. The system of claim 12, wherein the heat exchanger includes means for both heating and cooling the cardioplegic solution, and the control means also controls the heating and cooling means.

19. The system of claim 12, wherein the pump comprises an in-line bladder and a drive means for changing the volume of the bladder.

20. The system of claim 12, wherein said control means controls the pump to provide a fill cycle for filling the pump chamber of the pump, which fill cycle comprises two separate time segments including a first period for introduction of blood from the conduit and a second period for introduction of the second fluid, whereby the blood and second fluid are combined in the pump chamber in a selected ratio before being forwarded from the pump.

21. The system of claim 12, further comprising a heat exchanger for controlling fluid temperature in the cardioplegia delivery line, wherein the control means also controls the heat exchanger, and operates upon selection by the user of a desired temperature to adjust the heating and cooling of the cardioplegic solution in the heat exchanger to obtain the selected desired temperature.

22. The system of claim 1, wherein the control means operates to monitor pressure resulting from the pumped cardioplegic solution so that the monitored pressure is maintained within selected or predetermined pressure limits.

23. A clinical multi-fluid pumping system comprising:
  (a) a patient delivery line;
  (b) a first pump for pumping a first blood-containing fluid comprising a mixture of blood and a third fluid into the patient delivery line, said first pump being adapted to deliver said blood and third fluid in a variable ratio;
  (c) a second pump for delivering a second fluid into the delivery line downstream from the first pump at a flow rate less than 10% of the flow rate of the output from the first pump; and
  (d) control means for: adjusting the total volumetric rate of flow from the first pump; adjusting the ratio of blood to third fluid delivered by the first pump; and controlling the operation of the second pump so that the volumetric rate of flow of the second fluid is automatically maintained at a selected percentage of the flow rate from the first pump at all adjusted volumetric rates of flow from the first pump.

24. The system of claim 23, wherein said first pump employs two pumping chambers, so that one chamber may be refilled while the other is emptying, whereby substantially continuous flow from the first pump may be achieved.

25. The system of claim 23, further comprising a heat exchanger in the patient delivery line downstream from the second pump, which includes means for both heating and cooling the combined output of the pumps, and the control means also controls the heating and cooling means.

26. The system of claim 23, wherein the first pump comprises at least one disposable in-line bladder and a drive means for changing the volume of the bladder.

27. The system of claim 26, wherein the control means controls the first pump to provide a fill cycle for filling the bladder of the first pump which cycle comprises two separate time segments including a first period for introduction of blood from the conduit and a second period for introduction of the third fluid, whereby the blood and third fluid are combined in the bladder in a selected ratio before being forwarded from the first pump.

28. The system of claim 23, wherein the control means operates, upon selection by the user of a volumetric flow rate from the first pump, to establish the flow rate of the second pump.

29. The system of claim 23, further comprising a heat exchanger receiving the combined output of the pumps, and wherein the control means controls the heat exchanger and operates upon selection by the user of a desired temperature to adjust the heating and cooling by the heat exchanger to obtain the selected desired temperature.

30. The system of claim 23, wherein the control means operates to monitor pressure resulting from the cardioplegic solution so that the monitored pressure is maintained within selected or predetermined pressure limits.

31. A cardioplegia system for delivering cardioplegic solution comprising at least first and second fluids to the heart through a cardioplegic delivery line during open heart surgery in cooperation with an extracorporeal blood circuit employing a heart/lung machine, comprising:
   (a) a cardioplegic delivery line;
   (b) a first pump for pumping a first fluid into the cardioplegic delivery line;
   (c) a second pump for delivering a second fluid adapted to inhibit the action of the heart into the delivery line downstream from the first pump at a flow rate less than 10% of the flow rate of the output from the first pump; and
   (d) control means for: adjusting the total volumetric rate of flow from the first pump; and controlling the operation of the second pump so that the volumetric rate of flow of the second fluid is automatically maintained at a selected percentage of the flow rate from the first pump at all adjusted volumetric rates of flow from the first pump by automatically resetting the volumetric rate of flow from the second pump at any time the volumetric rate of flow from the first pump is changed.

32. A cardioplegia system for delivering cardioplegic solution comprising blood and at least second and third fluids to the heart through a cardioplegic delivery line during open heart surgery in cooperation with an extracorporeal blood circuit employing a heart/lung machine, comprising:
   (a) a conduit diverting a portion of the blood flow from the heart/lung machine to the cardioplegia delivery line;
   (b) a heat exchanger for controlling fluid temperature in the cardioplegia delivery line;
   (c) a first pump for combining the blood from the conduit with the second fluid and delivering the combined flow into the delivery line leading to the heat exchanger;
   (d) a second pump for delivering the third fluid into the delivery line at a flow rate less than 5% of the flow rate of the combined output of the first pump; and
   (e) control means for adjusting the total volumetric rate of flow from the first pump, and for controlling the operation of the second pump so that the volumetric rate of flow of the third fluid is maintained at a selected percentage of the flow rate from the first pump.

33. The system of claim 32, wherein said first pump employs two pumping chambers, so that one chamber may be refilled while the other is emptying, whereby substantially continuous flow from the first pump may be achieved.

34. The system of claim 32, in which the control means is further characterized by being adapted to control the first pump to adjust the ratio of blood to second fluid delivered.

35. The system of claim 32, wherein the output of the second pump joins the delivery line downstream from the first pump.

36. The system of claim 32, wherein the heat exchanger includes means for both heating and cooling the cardioplegic solution, and the control means also controls the heating and cooling means.

37. The system of claim 32, wherein the first pump comprises at least one disposable in-line bladder and a drive means for changing the volume of the bladder.

38. The system of claim 37, wherein said control means controls the first pump to provide a fill cycle for filling the bladder of the first pump, which fill cycle comprises two separate time segments including a first period for introduction of blood from the conduit and a second period for introduction of the second fluid, whereby the blood and second fluid are combined in the bladder in a selected ratio before being forwarded from the first pump.

39. The system of claim 32, wherein the control means operates, upon selection by the user of a volumetric flow rate from the first pump, to establish the flow rate of the second pump.

40. The system of claim 32, wherein the control means also controls the heat exchanger, and operates upon selection by the user of a desired temperature to adjust the heating and cooling of the cardioplegic solution in the heat exchanger to obtain the selected desired temperature.

41. The system of claim 32, wherein the control means operates to monitor pressure resulting from the pumped cardioplegia solution so that the monitored pressure is maintained within selected or predetermined pressure limits.

42. A cardioplegia system for delivering cardioplegic solution comprising blood and at least second and third fluids to the heart through a cardioplegia delivery line during open heart surgery in cooperation with an extracorporeal blood circuit employing a heart/lung machine, comprising:
   (a) a conduit diverting a portion of the blood flow from the heart/lung machine to the cardioplegia delivery line;
   (b) a heat exchanger for adjusting fluid temperature in the cardioplegia delivery line;
   (c) a first pump for combining the blood from the conduit with the second fluid and delivering the combined flow into the delivery line leading to the heat exchanger;
   (d) a second pump for delivering the third fluid into the delivery line at a flow rate less than 10% of the flow rate of the combined output of the first pump; and
   (e) control means for adjusting the ratio of blood and second fluid delivered by the first pump, and for adjusting the total volumetric rate of flow from the first pump, and for controlling the operation of the second pump so that the volumetric rate of flow of the third fluid is maintained at a selected percentage of the flow rate from the first pump.

43. The system of claim 42, wherein said first pump comprises a pump chamber having an inlet and an outlet, and drive means for varying the volume of the pump chamber.

44. The system of claim 42, wherein said first pump employs two pumping chambers, so that one chamber may be refilled while the other is emptying, whereby substantially continuous flow from the first pump may be achieved.

45. The system of claim 42, wherein the third fluid is a potassium solution and the second pump is a device for delivering the potassium solution into the delivery line downstream from the first pump.

46. The system of claim 42, wherein the heat exchanger includes means for both heating and cooling the cardioplegic solution, and the control means also controls the heating and cooling means.

47. The system of claim 42, wherein the first pump comprises at least one disposable in-line bladder and a separate drive means for changing the volume of the bladder.

48. The system of claim 47, wherein said control means controls the first pump to provide a fill cycle for filling the bladder of the first pump, which fill cycle comprises two separate time segments including a first period for introduction of blood from the conduit and a second period for introduction of the second fluid, whereby the blood and second fluid are combined in the bladder in a selected ratio before being forwarded from the first pump.

49. The system of claim 42, wherein the control means operates, upon selection by the user of a volumetric flow rate from the first pump, to establish the flow rate of the second pump.

50. The system of claim 42, wherein the control means also controls the heat exchanger, and operates upon selection by the user of a desired temperature to adjust the heating and cooling of the cardioplegic solution in the heat exchanger to obtain the selected desired temperature.

51. The system of claim 42, wherein the control means operates to monitor pressure resulting from the pumped cardioplegia solution so that the monitored pressure is maintained within selected or predetermined pressure limits.

52. A cardioplegia system for delivering cardioplegic solution comprising blood and at least a second fluid to the heart through a cardioplegia line during open heart surgery in cooperation with an extracorporeal blood circuit employing a heart/lung machine, comprising:
(a) a conduit diverting a portion of the blood flow from the heart/lung machine to the cardioplegia delivery line;
(b) a heat exchanger for controlling fluid temperature in the cardioplegia delivery line;
(c) a pump in the delivery line upstream from the heat exchange for accurately delivering a plurality of fluids in selected ratios, comprising:
(i) at least one pumping chamber;
(ii) drive means for altering the volume of the pumping chamber;
(iii) a first valved inlet for conveying blood from the conduit to the pumping chamber;
(iv) a second valved inlet for conveying the second fluid to the pumping chamber;
(v) a valved outlet for conveying fluid from the pumping chamber toward the heat exchanger; and
(vi) control means for the drive means, the inlets and the outlet for admitting said blood and second fluid to the pumping chamber for delivery to the outlet in a selected ratio, whereby the control means may be adjusted to vary the ratio of blood and second fluid delivered through the outlet.

53. The system of claim 52, wherein said pump employs two pumping chambers, so that one chamber may be refilled while the other is emptying, whereby substantially continuous flow from the pump may be achieved.

54. The system of claim 52, wherein the pump comprises at least one disposable in-line bladder and the drive means is separable from the bladder and changes the volume of the bladder.

55. The system of claim 54, wherein the control means controls the pump to provide a fill cycle for filling the bladder of the pump, which fill cycle comprises two separate time segments, including a first period for introduction of blood from the conduit and a second period for introduction of the second fluid, whereby the blood and second fluid are combined in the bladder in a selected ratio before being forwarded from the pump.

56. The system of claim 52, wherein the cardioplegia solution contains a potassium solution in addition to the blood and second fluid and further comprising a second pump for proportioning the potassium solution into the delivery line, and wherein the control means controls the second pump to provide a flow rate therefrom which is a selected percentage of the output of the first pump.

57. The system of claim 56, wherein the control means operates, upon selection by the user of a volumetric flow rate from the first pump and selection of a concentration of potassium, to establish the flow rate of the second pump.

58. The system of claim 57, wherein the output of the second pump joins the delivery line downstream from the first pump.

59. The system of claim 52, wherein the heat exchanger includes means for both heating and cooling the cardioplegic solution, and the control means also controls the heating and cooling means.

60. The system of claim 52, wherein the control means also controls the heat exchanger and operates upon selection by the user of a desired temperature to adjust the heating and cooling of the cardioplegic solution in the heat exchanger to obtain the selected desired temperature.

61. The system of claim 52, wherein the control means operates to monitor pressure resulting from the cardioplegic solution so that the monitored pressure is maintained within selected or predetermined pressure limits.

62. A cardioplegia system for delivering cardioplegic solution comprising blood and at least a second fluid to the heart through a cardioplegia delivery line during open heart surgery in cooperation with an extracorporeal blood circuit employing a heart/lung machine, comprising:
(a) a conduit diverting a portion of the blood flow from the heart/lung machine to the cardioplegia delivery line;

(b) a heat exchanger for controlling fluid temperature in the cardioplegia delivery line;

(c) a pump for receiving the blood from the conduit and the second fluid and forwarding the combined flow through the heat exchanger, the pump comprising:
  (i) an inlet;
  (ii) an outlet;
  (iii) a first pumping bladder between the inlet and the outlet;
  (iv) a second pumping bladder in parallel with the first pumping bladder;
  (v) a first drive for changing the volume of the first bladder;
  (vi) a second drive for changing the volume of the second bladder;
  (vii) valve means controlling fluid communication between the inlet and each of the bladders, and between each of the bladders and the outlet; and
  (viii) control means for controlling the valve means and the first and second drives so that, at first times, the first drive is reducing the first bladder volume and forcing fluid therefrom through the outlet and the second drive is expanding the volume of the second bladder so that fluid is filling the bladder from the inlet, and, at second times, the second drive is reducing the second bladder volume and forcing fluid therefrom through the outlet and the first drive is expanding the volume of the first bladder so that fluid is filling the bladder from the inlet.

63. The system of claim 62, wherein the control means controls the pump to provide a fill cycle for filling each bladder of the pump, each of which fill cycles comprises two separate time segments, including a first period for introduction of blood from the conduit and a second period for introduction of the second fluid, the blood and second fluid are combined in the bladder in a selected ratio before being forwarded from the pump.

64. The system of claim 62, wherein the cardioplegia solution contains a potassium solution in addition to the blood and second fluid and a second pump delivers the potassium solution to the delivery line, and the control means adjusts the output rate of the second pump to a selected percentage of the output of the first pump.

65. The system of claim 64, wherein the output of the second pump joins the delivery line downstream from the first pump.

66. The system of claim 64, wherein the control means operates, upon selection by the user of a volumetric flow rate from the first pump, to establish the flow rate of the second pump.

67. The system of claim 62, wherein the heat exchanger includes means for both heating and cooling the cardioplegic solution, and the control means also controls the heating and cooling means.

68. The system of claim 62, wherein the control means also controls the beat exchanger and operates upon selection by the user of a desired temperature to adjust the heating and cooling of the cardioplegic solution in the heat exchanger to obtain the selected desired temperature.

69. The system of claim 62, wherein the control means operates to monitor pressure resulting from the pumped cardioplegia solution so that the monitored pressure is maintained within selected or predetermined pressure limits.

* * * * *